(12) United States Patent
Lin et al.

(10) Patent No.: US 8,221,138 B2
(45) Date of Patent: Jul. 17, 2012

(54) AUDIO JACK CONNECTOR WITH IMPROVED SOLDERING TAIL

(75) Inventors: Kuo-Lung Lin, Tu-Cheng (TW); Kuo-Chun Hsu, Tu-Cheng (TW)

(73) Assignee: Hon Hai Precision Ind. Co., Ltd., New Taipei (TW)

( * ) Notice: Subject to any disclaimer, the term of this patent is extended or adjusted under 35 U.S.C. 154(b) by 389 days.

(21) Appl. No.: 12/534,793

(22) Filed: Aug. 3, 2009

(65) Prior Publication Data

US 2010/0144213 A1 Jun. 10, 2010

(30) Foreign Application Priority Data

Dec. 9, 2008 (TW) .................................. 97222016

(51) Int. Cl.
*H01R 13/428* (2006.01)

(52) U.S. Cl. .......................................... 439/83; 439/744

(58) Field of Classification Search .................. 439/744, 439/669, 668, 83
See application file for complete search history.

(56) References Cited

U.S. PATENT DOCUMENTS

| | | | | |
|---|---|---|---|---|
| 7,101,230 B2 * | 9/2006 | Ma | .................................. | 439/668 |
| 7,470,153 B2 * | 12/2008 | Han et al. | ....................... | 439/669 |
| 7,568,954 B2 * | 8/2009 | Li et al. | .......................... | 439/668 |
| 2009/0149080 A1 * | 6/2009 | Wu | .................................. | 439/668 |

FOREIGN PATENT DOCUMENTS

| | | |
|---|---|---|
| CN | 2667743 Y | 12/2004 |
| JP | 2872023 | 1/1999 |

* cited by examiner

*Primary Examiner* — Tulsidas C Patel
*Assistant Examiner* — Travis Chambers
(74) *Attorney, Agent, or Firm* — Wei Te Chung; Andrew C. Cheng; Ming Chieh Chang

(57) ABSTRACT

An electrical connector (100) includes an insulative housing (1) and at least one contact (2) retained in the housing. The housing includes a base portion (11) and a mating portion (12) extending forwards from the base portion, and the base portion defines a mounting face (114) thereof and the mating portion defines a mating cavity (121) extending from a mating face (120) into the housing. The at least one contact defines a retaining portion (21) retained in the base portion, a resilient arm (22) extending from the retaining portion with a part projecting into the mating cavity and a soldering leg (23) arranged to parallel to the mounting face. The soldering leg is disposed within the scope of the mounting face and defines a first and a second soldering portion (231, 232) forming an angle therebetween.

20 Claims, 5 Drawing Sheets

US 8,221,138 B2

AUDIO JACK CONNECTOR WITH IMPROVED SOLDERING TAIL

BACKGROUND OF THE INVENTION

1. Field of the Invention

The present invention relates to an audio jack connector, and more particularly to an audio jack connector having contact with improved soldering tail facilitating reliable solder joint.

2. Description of the Related Art

Electrical connectors have been widely used in electrical equipments for interconnection. Chinese Utility Patent Number 2667743Y issued to Lin et al. on Dec. 29, 2004 discloses a typical electrical connector, which is mounted onto a printed circuit board and includes an insulative housing providing a plurality of contacts for interfacing with a mated connector. The housing defines a bottom face for mounting onto the printed circuit board and a mating face recessed with a mating cavity for receiving a mating connector therein. Each contact defines a retaining portion retained in the housing, an elastic arm extending from one side edge of the retaining portion and projecting into the mating cavity, and a soldering portion extending outwards and beyond the bottom face of the housing from another side edge of the retaining portion. However, the soldering portions extend beyond the bottom area of the housing and may exhaust a lot of space of the printed circuit board, which is not beneficial for miniaturization of both the electrical connector and the electrical equipment.

An improved design of contact tail is necessary and in which the exhaustion of the space of the printed circuit board is considerably reduced.

SUMMARY OF THE INVENTION

Accordingly, an object of the present invention is to provide an audio jack with improved contact tail for reducing the exhaustion of the space of the printed circuit board while maintaining a robust surface area for reliable solder joint thereon.

In order to achieve the object set forth, an electrical connector includes an insulative housing and at least one contact retained in the housing. The housing includes a base portion and a mating portion extending forwards from the base portion, and the base portion defines a mounting face thereof and the mating portion defines a mating cavity extending from a mating face into the housing. The contact defines a retaining portion retained in the base portion, a resilient arm extending from the retaining portion with a part projecting into the mating cavity and a soldering leg arranged to parallel to the mounting face. The soldering leg is disposed within the scope of the mounting face and defines a first and a second soldering portion forming an angle therebetween.

Other objects, advantages and novel features of the invention will become more apparent from the following detailed description of the present embodiment when taken in conjunction with the accompanying drawings.

DETAILED DESCRIPTION OF THE INVENTION

Figure 1:
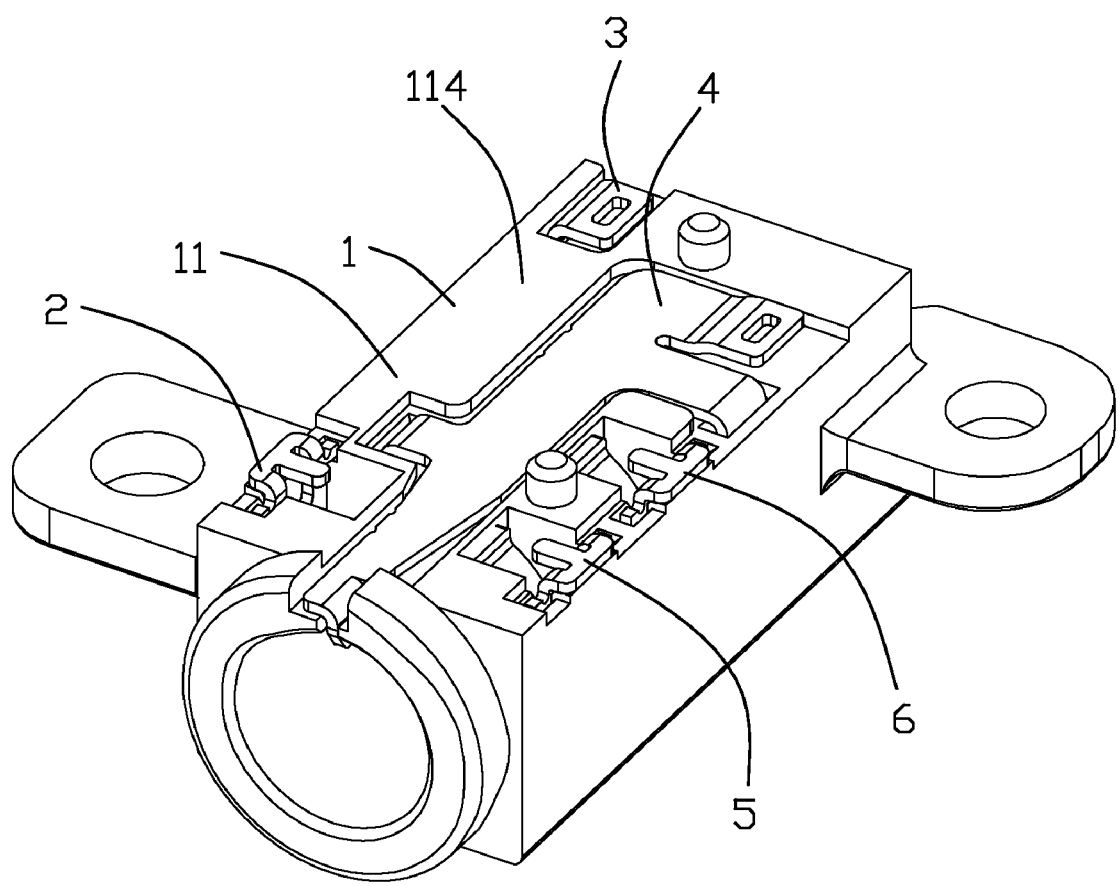
FIG. 1 is a perspective view of an electrical connector in accordance with a preferred embodiment of the present invention.

Reference will now be made to the drawing figures to describe a preferred embodiment of the present invention in detail.

Figure 2:
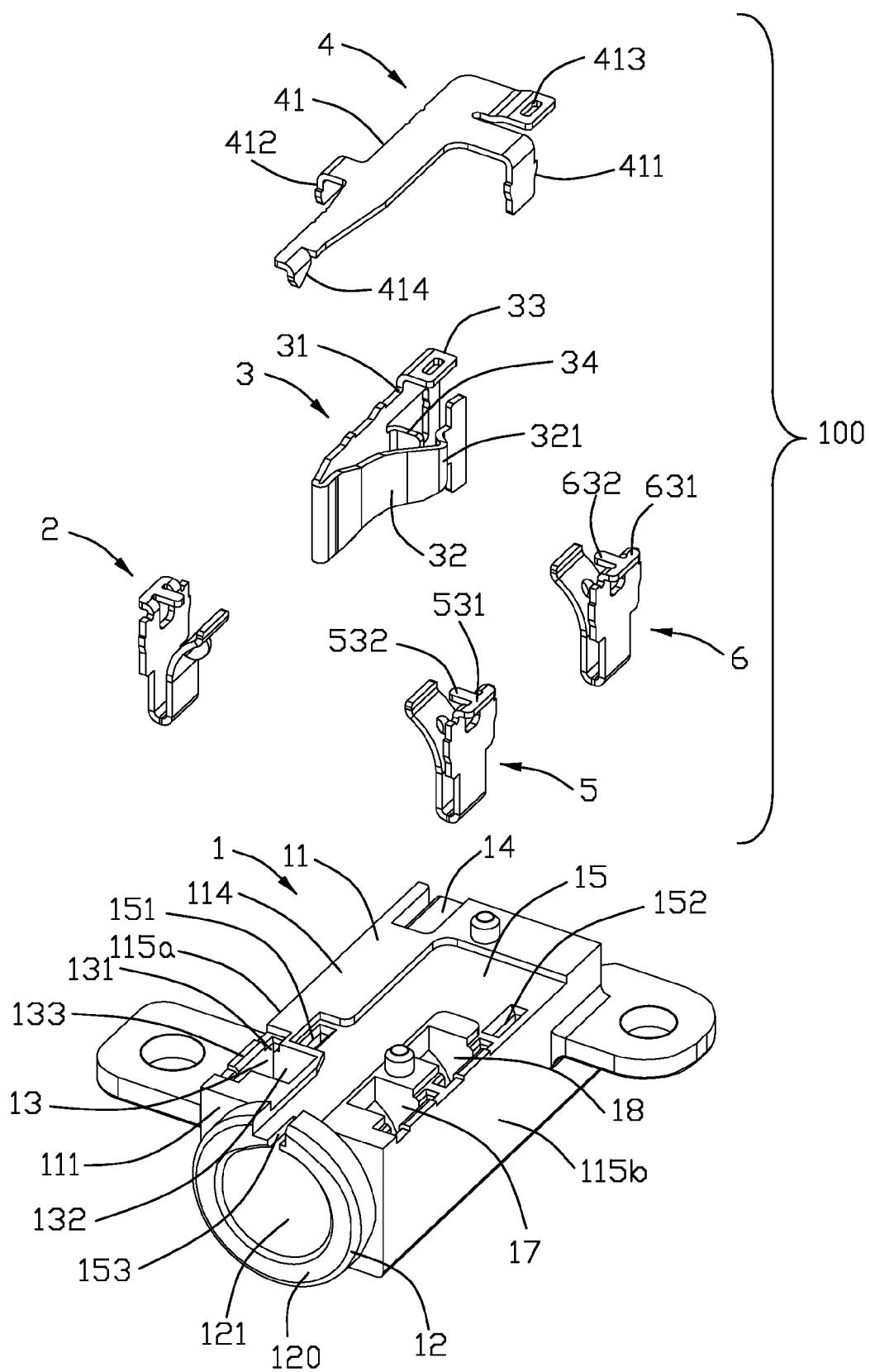
FIG. 2 is an exploded view of the electrical connector shown in FIG. 1.

Referring to FIG. 1 and FIG. 2, an electrical connector 100, preferably an audio jack for mounting onto a printed circuit board (not shown), includes an insulative housing 1 and a plurality of contacts retained in the housing.

Referring to FIG. 2, the housing 1 includes a rectangular base portion 11 and a cylindrical mating portion 12 extending forwards from the base portion 11. The base portion 11 defines a front face 111, a rear face opposite to the front face 111, a top wall perpendicular to the front face 111, a bottom face 114 opposite to the top wall and a pair of sidewalls 115a, 115b connecting with the top wall and the bottom face 114. The bottom face 114 is referred as a mounting face, and the mating portion 12 extends forwards from the front face 111 of the base portion 11. A columnar mating cavity 121 for receiving a mating connector (not shown) therein recesses rearwards from a mating face 120 of the mating portion 12 in a front-to-rear direction and is surrounded by the sidewalls 115a, 115b and the bottom and top faces. The sidewalls 115a, 115b are disposed at two opposite sides of the mating cavity 121.

Referring to FIG. 2, a plurality of receiving grooves for receiving the contacts therein are separately defined in the housing 1. The receiving grooves includes a first and second receiving grooves 13, 14 disposed at one sidewall 115a, a third receiving groove 15 disposed at the bottom face 114 of the housing, and a fourth and fifth receiving grooves 17, 18 disposed at the other sidewall 115b. The first receiving groove 13 recesses upwards from the bottom face 114 and provides a retaining slot 131 disposed in the sidewall 115a and a receiving portion 132 extending towards and communicating with the mating cavity 121. The second receiving groove 14 recesses forwards from the rear face of the housing 1 with a part running through the bottom face 114. The second receiving groove 14 is positioned behind the first receiving groove 13, and the both are disposed at one side of the mating cavity 121. The third receiving groove 15 recesses upwards from a middle portion of the mounting face 114 and has an L-shaped configuration, and a slot 153 adjacent to the mating face 120 for communicating the third receiving groove 15 with the mating cavity 121 is provided at a front end of the L-shaped portion. The fourth and fifth receiving grooves 17, 18 both located at the sidewall 115b and communicating with the mating cavity 121 have an identical configuration as the first receiving groove 13.

Figure 3:
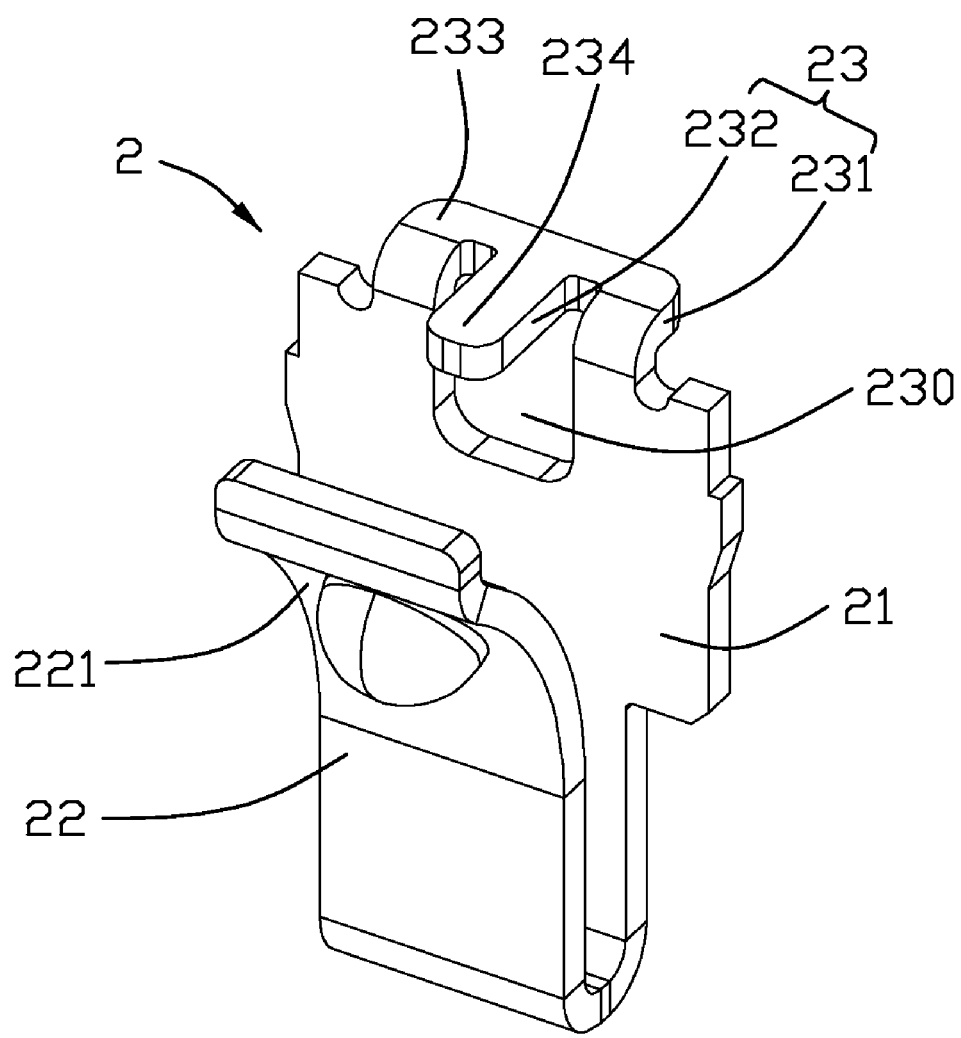
FIG. 3 is a perspective view of a first contact shown in FIG. 2.
Figure 4:
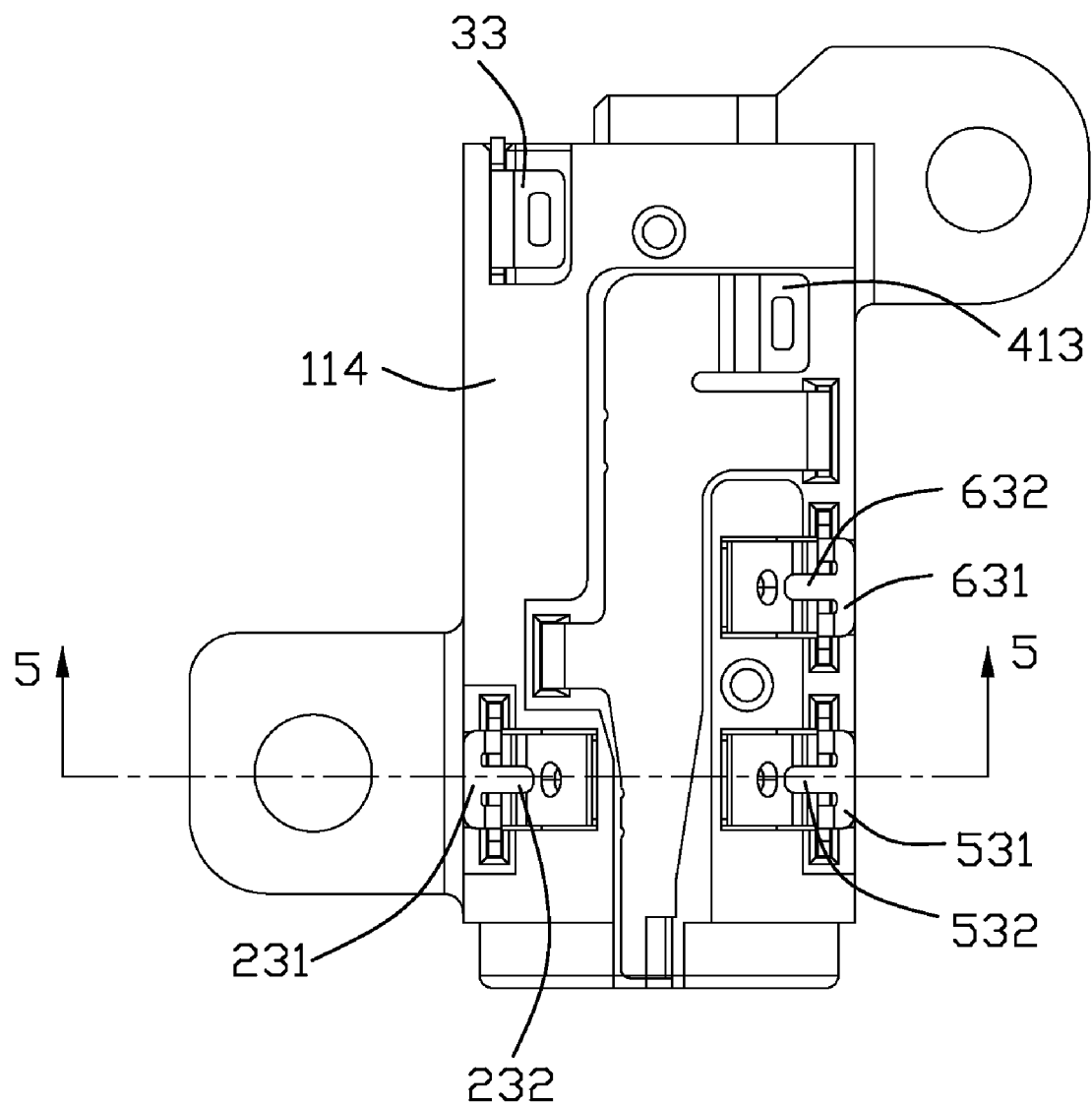
FIG. 4 is a bottom plan view of the electrical connector shown in FIG. 1.
Figure 5:
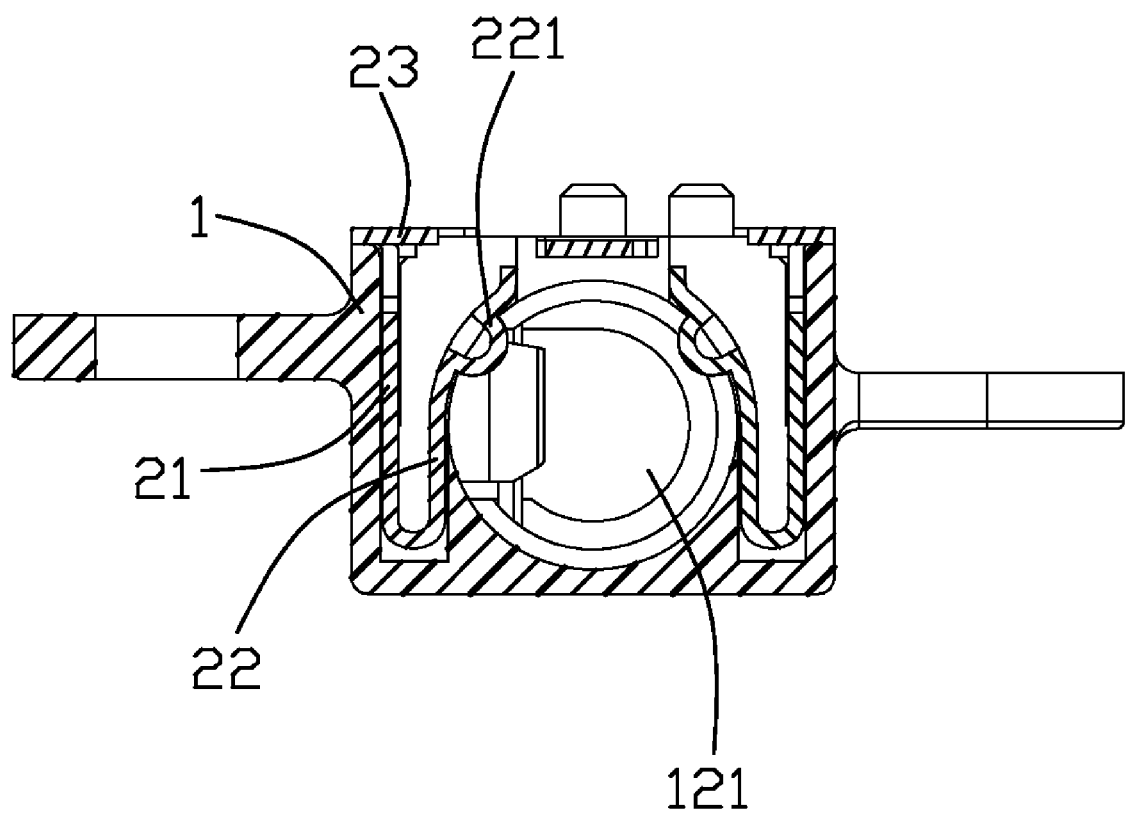
FIG. 5 is a cross-sectional view of the electrical connector taken along line 5-5 of FIG. 4.

Referring to FIG. 1 to FIG. 3, the contacts include a first contact 2 defining a board-shaped retaining portion 21 with bars at lateral sides thereof, a resilient arm 22 arranged to have a portion in parallel with the retaining portion 21, and with a tip extending away from the retaining portion, and a soldering leg 23 extending to the bottom face 114 and arranged to parallel to the bottom face 114 from the retaining portion 21. The free end of the resilient arm 22 projecting into the mating cavity 121 is defined as a contacting portion 221. The soldering leg 23 includes a first soldering portion 231 extending outwards from a lower edge of the retaining portion 21 and a second soldering portion 232 extending perpendicularly to the first soldering portion 231 from an inner side edge of the first soldering portion 231, and the first and second soldering portions 231, 232 extend in opposite direction. The second soldering portion 232 is formed by a metal piece punched out from the retaining portion 21 and arranged to parallel to the mounting face 114. A through hole 230 corresponding to the metal piece is provided at the retaining portion 21, and the second soldering portion 232 connects with an inner side edge of the first soldering portion 231 disposed in the through hole 230. The first soldering portion 231 is defined as a flat piece extending in a mating direction, and the soldering faces 233, 234 of the soldering leg 23 are disposed in a same plane and have a T-shaped configuration. In this embodiment, the first soldering portion 231 is perpendicular to the second soldering portion 232, and in other embodiments, any other angle can be arranged between the first soldering portion 231 and the second soldering portion 232.

Referring to FIGS. 1, 2, 4 and 5, the first contact 2 is inserted into the first receiving groove 13 from the mounting face 114. The retaining portion 21 is retained to the retaining slot 131 and the resilient arm 22 is received in the receiving portion 132 with the contacting portion 221 projecting into the mating cavity 121. The first soldering portion 231 abuts against a protrusion 133 extending downwards from the bottom face 114 of the sidewall 115a and does not extend beyond the sidewall 115a, and the second soldering portion 232 is disposed under the housing 1. The soldering leg 23 is disposed within the area of the mounting face 114, which is beneficial for miniaturization. Contacts 4, 5 have the identical configuration as the first contact 2, and the contacts 4, 5 are respectively retained in the fourth and fifth receiving grooves 17, 18.

Referring to FIGS. 1, 2, 4 and 5, a second contact 3 defines a blade-type retaining portion 31, a resilient arm 32 bending from a front side edge of the retaining portion 31 and extending rearwards to opposite to the retaining portion 31, and a soldering leg 33 extending horizontally towards the resilient arm 32 from a lower side edge of the retaining portion 31. The retaining portion 31 defines a supporting portion 34 punched from a middle portion thereof for supporting the resilient arm 32, and the resilient arm 32 defines a contacting portion 321 at a free end thereof. The soldering leg 33 and the resilient arm 32 are arranged at a same side of the retaining portion 31. The second contact 3 is inserted into the second receiving groove 14 from the rear face of the housing 1, and the contacting portion 321 projects into the mating cavity 121 and the soldering leg 33 arranged to parallel to the mounting face 114 is disposed within the scope of the mounting face 114.

Referring to FIG. 1 and FIG. 2, a third contact 4 defines a blade-shaped base portion 41, a pair of locking portions 411, 412 respectively extending upwards from two opposite side edges of the base portion 41 and a soldering leg 413 arranged to parallel to the mounting face 114 and disposed behind the locking portion 411. The base portion 41 provides a contacting portion 414 bending upwards from a front side edge thereof for contacting with the mating connector, and the soldering leg 413 and the locking portion 411 are disposed at a same side edge of the base portion 41. The third contact 4 is retained to the mounting face 114 by the locking portions 411, 412 respectively engaging with the retaining holes 151, 152 disposed at the bottom face 114 of the housing 1. The base portion 41 is received in the third receiving groove 15, and the contacting portion 414 projects into the mating cavity 121 through the slot 153, and the soldering leg 413 is arranged within the scope of the mounting face 114. The soldering legs 23, 33, 413, 53, 63 all disposed within the scope of the mounting face 114 may save the soldering space of the printed circuit board, which benefits miniaturization. Moreover, the second soldering portions 232, 532, 632 are respectively punched from the corresponding retaining portions instead of extending from an extra metal piece, which may reduce the cost of the electrical connector.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An electrical connector comprising:
    an insulative housing having a base portion and a mating portion extending forwards from the base portion, the base portion defining a mounting face thereof and the mating portion defining a mating cavity extending from a mating face into the housing; and
    at least one contact retained in the housing and each defining a retaining portion retained in the base portion, a resilient arm extending from the retaining portion with a part projecting into the mating cavity and a soldering leg arranged to parallel to the mounting face, the soldering leg disposed within the scope of the mounting face and defining a first and a second soldering portion forming an angle therebetween,
    wherein the first soldering portion bends outwards from a side edge of the retaining portion and the second soldering portion extends inwards from an inner side edge of the first soldering portion,
    wherein the second soldering portion is punched from the retaining portion and the two soldering portions are arranged in a same plane.

2. The electrical connector as described in claim 1, wherein the first soldering portion elongates in a mating direction and the second soldering portion extends perpendicularly to the mating direction.

3. The electrical connector as described in claim 2, wherein the soldering leg is featured a T-shaped configuration.

4. The electrical connector as described in claim 1, wherein the first soldering portion sandwiches the second soldering portion along a direction defined by the side edge of the retaining portion.

5. The electrical connector as described in claim 1, wherein the retaining portion provides a through hole corresponding to the second soldering portion thereon, and the second soldering portion extends from an inner side edge of the first soldering portion disposed in the through hole.

6. An electrical connector comprising:
    an insulative housing having a mating face, a mounting face adjacent to the mating face, a mating cavity recessed rearwards from the mating face thereof and at least one receiving groove disposed at a sidewall of the mating cavity and communicating with the mating cavity; and
    at least one contact received in the housing and each defining a retaining portion retained in the receiving groove, a resilient arm extending from the retaining portion with a part projecting into the mating cavity and a soldering leg with a part punched from the retaining portion disposed to parallel to the mounting face,
    wherein the soldering leg is arranged within the scope of the mounting face,
    wherein the soldering leg defines a first soldering portion bending outwards from a side edge of the retaining portion and a second soldering portion extending inwards from a side edge of the first soldering portion.

7. The electrical connector as described in claim 6, wherein the first soldering portion sandwiches the second soldering portion along a direction defined by the side edge of the retaining portion.

8. The electrical connector as described in claim 6, wherein the second soldering portion is punched from the retaining portion, and the first and second soldering portions are arranged in a same plane.

9. The electrical connector as described in claim 8, wherein the retaining portion defines a through hole corresponding to the second soldering portion thereon, and the second soldering portion extends from a side edge of the first soldering portion disposed in the through hole.

10. An electrical connector comprising:
an insulative housing defining an exposed mating face into which a mating cavity extends inwardly for mating with a complementary connector, and a bottom mounting face, for mounting to a printed circuit board, into which a contact receiving groove upwardly extends; and
a contact upwardly assembled into the contact receiving groove from the mounting face with a main body, from which a resilient contact portion extends into the mating cavity and a horizontal solder leg extends essentially horizontally from thereof a root section joined with the main body, wherein said horizontal solder leg includes a first solder portion extending from the root section in a first transverse direction and defining opposite outer and inner edges thereof under condition that the inner edge is closer to the root section than the outer edge, and further includes a second solder portion extending from the inner edge in a second transverse direction opposite to said first transverse direction and defining a tip under condition that the tip of the second solder portion and the outer edge of the first solder portion are located by two sides of the root section in said first transverse direction.

11. The electrical connector as claimed in claim 10, wherein the first transverse directs away from the housing.

12. The electrical connector as claimed in claim 11, wherein the second solder portion is essentially aligned with the contact receiving groove in a vertical direction while the first solder portion is not.

13. The electrical connector as claimed in claim 12, wherein the first solder portion is supported by the bottom mounting face of the housing while the second solder portion is not.

14. The electrical connector as claimed in claim 10, wherein the mating face is a front face of the housing and the mating cavity extends rearwardly into the housing.

15. The electrical connector as claimed in claim 10, wherein the first solder portion is dimensioned larger than the second solder portion in a longitudinal direction perpendicular to both said first transverse direction and said second transverse direction.

16. The electrical connector as claimed in claim 10, wherein said main body includes a vertical retaining portion where the root section is joined.

17. The electrical connector as claimed in claim 16, wherein said retaining portion defines a through hole corresponding to the second solder portion.

18. The electrical connector as claimed in claim 10, wherein said outer edge of the first solder portion and said tip of the second solder portion are spaced from the root section with substantially a same distance in the first transverse direction.

19. The electrical connector as claimed in claim 10, wherein the first solder portion sandwiches the second solder portion along a direction defined by said inner edge.

20. The electrical connector as claimed in claim 19, wherein the first solder portion is symmetrically located by two sides of the second solder portion along said direction.

* * * * *